United States Patent
Leventis et al.

[11] Patent Number: 5,796,345
[45] Date of Patent: Aug. 18, 1998

[54] APPARATUS FOR DETECTING MOISTURE IN GARMENTS

[76] Inventors: Nicholas Leventis, 1604 McCutchen Dr., Rolla, Mo. 65401; William A. Galison, 210 Thompson St., New York, N.Y. 10012

[21] Appl. No.: 783,584

[22] Filed: Jan. 13, 1997

[51] Int. Cl.[6] .................................................. G08B 21/00
[52] U.S. Cl. ........................... 340/604; 340/605; 429/118
[58] Field of Search ........................... 340/604, 603, 340/605, 573, 622; 429/224, 118, 207, 206, 127, 218, 90, 233

[56] References Cited

U.S. PATENT DOCUMENTS

| | | | |
|---|---|---|---|
| 3,199,095 | 8/1965 | Ashida | 340/604 |
| 3,460,123 | 8/1969 | Bass . | |
| 3,508,235 | 4/1970 | Baisden | 304/604 |
| 3,914,813 | 10/1975 | Berchielli et al. | 429/27 |
| 4,205,672 | 6/1980 | Dvorak . | |
| 4,356,818 | 11/1982 | Macias et al. . | |
| 4,522,897 | 6/1985 | Walsh | 429/119 |
| 4,704,108 | 11/1987 | Okada et al. | 604/361 |
| 5,025,247 | 6/1991 | Banks | 340/573 |
| 5,264,830 | 11/1993 | Kline et al. . | |
| 5,266,928 | 11/1993 | Johnson . | |
| 5,311,100 | 5/1994 | Brain | 315/129 |
| 5,395,358 | 3/1995 | Lu . | |
| 5,469,145 | 11/1995 | Johnson . | |
| 5,469,146 | 11/1995 | Gurler . | |

OTHER PUBLICATIONS

Steven S. Zumdahl, *Chemical Principles*, Chapter 11 –Electrochemistry, Section 11.5 –Batteries, (1992 D.C. Heath and Company, Lexington, Massachusetts), pp. 444–446.

*Primary Examiner*—Jeffery A. Hofsass
*Assistant Examiner*—Sihong Huang
*Attorney, Agent, or Firm*—Theodore F. Shiells

[57] ABSTRACT

This invention describes a sensing device useful as a wet condition indicator, and is composed of a sensing element that produces electric energy when it becomes wet, and an informing means such as an integrated circuit/piezoelectric buzzer (speaker), light source or electrochromic device. The sensing element incorporates small amounts of non-toxic, non-allergenic substances and operates as a battery when wet. That battery produces enough electric energy to power the informing device without need of any other circuitry or batteries. This has the advantage of lower cost so that it can be used for a wet condition indicator in disposable diapers. One sensing element is incorporated in each diaper, and can be discarded with it, while the informing element is reused.

28 Claims, 2 Drawing Sheets

APPARATUS FOR DETECTING MOISTURE IN GARMENTS

TECHNICAL FIELD

This invention relates to an apparatus for detecting wet garments. More particularly, the invention relates an apparatus including a power supply element that operates as an electrochemical cell only when wet to power an indicator such as an audible alarm, light source or electrochromic device.

BACKGROUND OF THE INVENTION

It is well known that prolonged contact of soiled diapers with the skin causes a diaper rash. This is a painful condition best prevented by changing the diaper as soon as it gets soiled, rather than treating it with medication later. However, generally the parent or care giver for a child may not be made aware that a diaper is soiled or wet until the diaper has been wet for some time. This increases the risk of diaper rash.

In addition, with modern disposable diapers, it is frequently difficult to tell that a diaper has been wetted until the diaper has been removed. This is also the case with adult diapers, since adults with incontinence problems may leak at a low rate continuously and therefore not have a clear indication of when a diaper is wet enough to require changing until the diaper is checked. However, once a diaper has been removed, there may be a tendency to replace it "just to be sure", even if it is not wet. This practice is uneconomical and tends to unnecessarily increase solid waste. Accordingly, it would be preferable to be alerted to the wet or dry condition of the diaper prior to removal.

Several patents describe alarm devices, all designed to assist parents or attendants identify a wet diaper condition early on. These devices produce either a visual or an audible signal. In nearly all cases, these devices rely upon a conventional battery for power. In addition, these devices typically measure resistance or capacitance changes, creating the significant disadvantage that these values have to be monitored continuously, thus using electric power. Also, one has to use a comparator circuit in addition to the circuit that produces the audio or visual signal, as well as the one or more batteries needed to power the entire assembly. Accordingly, the cost of these wet condition indicator devices is high because batteries and comparator circuitry are needed.

U.S. Pat. No. 3,508,235 to Baisden suggests the use of two safety pins or separate sections of a single pin made of dissimilar metals (as examples are given zinc and silver) which are said to generate galvanic potential when both come in contact with urine. However, safety pins are not typically necessary or used on modern disposable diapers and, if used, have a relatively high manufacturing cost. Further, the normal locations for placement of safety pins are at the upper sides or front of a diaper. Since these locations are generally the last to be wetted, the diaper may be wet on the bottom for a considerable period of time before any wetness contacts the safety pins. Safety pins cannot practically be placed in the area of a diaper most likely to be wetted first, i.e., the bottom, owing to discomfort. Furthermore, the ability of these devices to operate as galvanic cells is limited on physical grounds. In order to create a galvanic cell one needs two substances: one in the oxidized form and one in the reduced form. In the U.S. Pat. No. 3,508,235 patent both substances are in the reduced form because they are metals. Urine is mildly acidic (pH~5.5) and, accordingly, there is a very low concentration of protons which may play the role of the oxidized form of the second redox couple needed for a galvanic cell, with Zn playing the role of the reduced form. A cell composed of two electrodes, one of zinc and one of silver dipped in urine will produce the theoretically expected voltage for the following cell (written in standard electrochemical notation: $Zn/Zn^{2+}$ ($<10^{-5}M$), other urine components (e.g., urea, uric acid, etc.), $H^+(10^{-5.5}M)/H_2/Ag$ that is ~0.7 V with silver appearing as the positive electrode. However, 0.7 V is not high enough to power typical integrated circuit/piezoelectric buzzer device.

Accordingly, there is a continuing need for an audible or visible indicator of wet garments that is safe, low cost, and easy to use. The present invention is primarily directed to providing such a device.

SUMMARY OF THE INVENTION

This need is met in accordance with a preferred embodiment of the present invention which provides a moisture detector for garments having a water-activated electrochemical cell and an informing means electrically connected to the electrochemical cell for indicating when the electrochemical cell is activated.

In accordance with a preferred aspect of this embodiment, the informing means is a piezoelectric speaker.

In accordance with a preferred aspect of this embodiment, the informing means is a light source.

In accordance with a preferred aspect of this embodiment, the informing means is an electrochromic indicator.

In accordance with a preferred aspect of this embodiment, the electrochemical cell has a porous separator having a first side and a second side to the separator having a conductive coating on at least one of the sides; a substantially oxidized chemical attached to the first side of the separator; and a substantially reduced chemical attached to the second side of the separator.

In accordance with a preferred aspect of this embodiment, the conductive coating is a conductor selected from the group consisting of carbon, gold, platinum and chromium and mixtures thereof.

In accordance with a preferred aspect of this embodiment, the substantially oxidized chemical is a mixture of $MnO_2$, carbon, $KHSO_4.xH_2O$ and a water based glue.

In accordance with a preferred aspect of this embodiment, the substantially oxidized chemical is a mixture of $KH_2PO_4.xH_2O$ and a water based glue.

In accordance with a preferred aspect of this embodiment, the substantially reduced chemical is a metal selected from the group consisting of zinc and aluminum and mixtures thereof.

In accordance with a preferred aspect of this embodiment, the porous separator is a microfiltration separator or filter paper.

In accordance with a preferred aspect of this embodiment, the electrochemical cell has a porous separator having a first side and a second side to the separator being folded to form a pocket such that the first side is on the inner surface of the pocket; a conductive coating on said first side; a substantially oxidized chemical in the pocket; and a substantially reduced chemical attached to the second side.

In accordance with another preferred embodiment of the present invention, a disposable undergarment that indicates a soiled or wet condition is provided, having a substantially water impermeable pant; absorbent material disposed on a first side of the pant; a water-activated electrochemical cell positioned within the absorbent material; means for informing attached to a second side of the pant; and means for electrically connecting the electrochemical cell to the means for informing.

In accordance with another embodiment of the present invention, a location aid for use with an emergency flotation device is provided having a water-activated electrochemical cell attached to the flotation device such that the electrochemical cell becomes wet when the flotation device is being used for flotation; means for informing attached to the flotation device; and means for electrically connecting the electrochemical cell to the means for informing.

BRIEF DESCRIPTION OF THE DRAWINGS

For a more complete understanding of the present invention and the advantages thereof, reference is made to the following detailed description taken in conjunction with the accompanying drawings wherein.

DETAILED DESCRIPTION OF THE PREFERRED EMBODIMENTS

According to the present invention, there is provided a low cost, non-toxic and non-allergenic detector of soiled or wet garments. Due to the small size and non-toxic nature of the invention, it can be used to detect moisture in, for instance, baby diapers, adult diapers, socks to prevent possible frostbite or anywhere else it is desirable to receive an early warning of a wet condition in an economically feasible way.

Unlike previous diaper wetness detectors, the present invention uses a combined sensor and power source that will hereinafter be referred to as the "sensor." Therefore, no separate battery is required. This is because the sensor is basically an electrochemical cell that is essentially electrochemically inactive when "dry" and only produces significant current when wet. Accordingly, when the sensor is placed in a area where it is desirable to be able to detect a wet state, such as the absorbent layer of a baby's diaper, the urine or other water containing substance (perspiration, fecal matter, etc.) activates the battery to produce electric power that is then available to operate an informing device such as a piezoelectric speaker, buzzer, light or electrochromic device.

The sensor is incorporated into the garment along with electrical connections both of which can be disposed of along with the garment. The informing means can also be permanently attached as in the case of a single use electrochromic device or it can be removable to permit repeated use. In the latter embodiment, the informing means can be fastened into a button or clip that can also serve to fasten the garment to the wearer.

The invention may also be used in a moisture detector for use in life vests or other flotation devices where it is desirable to have a strobe or other locating means automatically activate when the flotation device is in the water.

Figure 1:
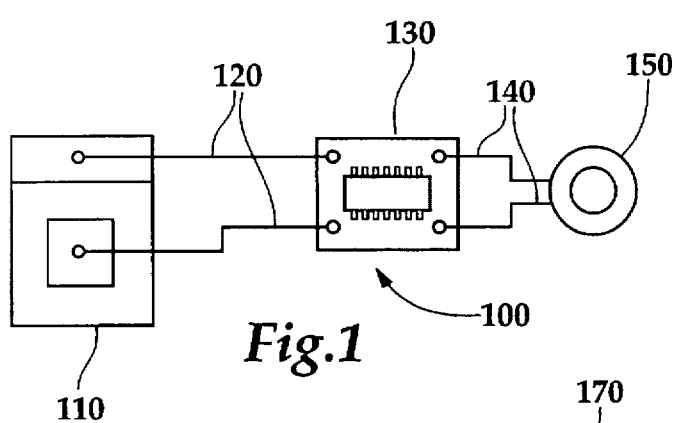
FIG. 1 is a simplified flattened view of a moisture detector according to a preferred embodiment of the invention.

Referring now in more detail to the drawings, in which like numerals refer to like parts throughout the several views, FIG. 1 illustrates a flattened view of a preferred embodiment of a device 100 to detect moisture in an undergarment according to a preferred embodiment of the present invention. The detector 100 comprises a sensor 110 connected by wires 120, or other suitable means known in the art, to an integrated circuit 130. The integrated circuit 130 is any of a number well known in the art that generates a musical or other audible signal. Such devices are affordable and well known for such applications as, for example, the playing of a tune when a greeting card is opened. With continued reference to FIG. 1, the integrated circuit 130 is also electrically connected by wires 140 that convey the audible signal generated by the integrated circuit to an informing device 150; in this embodiment, a piezoelectric buzzer/speaker.

As previously described, the sensor 110 is an electrochemical cell that only produces significant current when wet. Thus, when the undergarment becomes wet the electrochemical cell that comprises the sensor 110 begins to produce current that is transmitted via wires or other electrical conduits 120 to the integrated circuit 130 that generates an audible signal, such as a tone or music, transmitted by other electrical conduits 140 to the piezoelectric informing device 150 which alerts the wearer of the undergarment or an attendant of the wet condition.

In another embodiment of the invention, the sensor 110 is electrically connected by conduits 120 directly to a piezoelectric buzzer 150.

In another embodiment the informing device 150 is a light emitting diode or other suitable light source. When the sensor 110 becomes wet, it produces current that is transmitted by electrical conduits 120 directly to the light source 150 causing it to light, alerting the wearer or attendant of a wet condition.

As the current output of the sensing device/ electrochemical cell 110 increases with increasing wetness up to a point, another embodiment allows for the determination of relative wetness. In this embodiment, the piezoelectric buzzer 150 becomes louder with increasing wetness. In another embodiment the light emitting diode 150 becomes brighter with increasing wetness.

Figure 2:
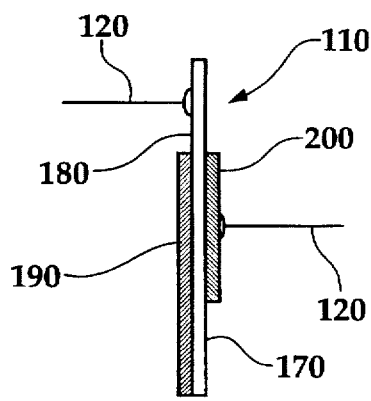
FIG. 2 is a cross-sectional view of a sandwich type detector according to a preferred embodiment of the invention.

Referring now to FIG. 2, there is shown a lateral view of a preferred embodiment of the sensor/electrochemical cell 110 of the present invention. It is essentially a sandwich construction of the various components. The middle is a porous separator 170, preferably filter paper, with a thin coating of a conductor 180. In a preferred embodiment carbon is the conductor 180, however other conductors such as gold may be used. They may be applied by, among other methods, sputtering or vacuum evaporation. The amount needed is very little, so the use of a more expensive conductor like gold would not be cost prohibitive. Of course, other conductors such as Al, Pt, Cr or a mix of any of these may also be used.

On one of the sides of a preferred embodiment of the sensor 110 is attached a mixture of substances 190 in the oxidized form comprising $MnO_2$, C, $KHSO_4.xH_2O$ with a water based glue such as UHU™. An alternative embodiment uses only the $KHSO_4$ attached to the electrode, but a lower voltage results. ($KH_2PO_4.xH_2O$ may also be used.) The relative amounts of the various substances used varies depending on the specific embodiment and output requirements; however, for example, the $MnO_2$:C ratio in a preferred embodiment is (w/w) from 100%:0% to 0.5%:99.5%. The Amount of $KHSO_4$ or $KH_2PO_4$ in a preferred embodiment is from 0.001 grams to more than 1 gram and the amount of glue may be from 0.001 gram to more than 0.1 gram.

On the other side of the same embodiment is a metal in a reduced form 200. This metal is preferably zinc or aluminum however, other suitable materials will occur to those skilled in the art.

Figure 3:
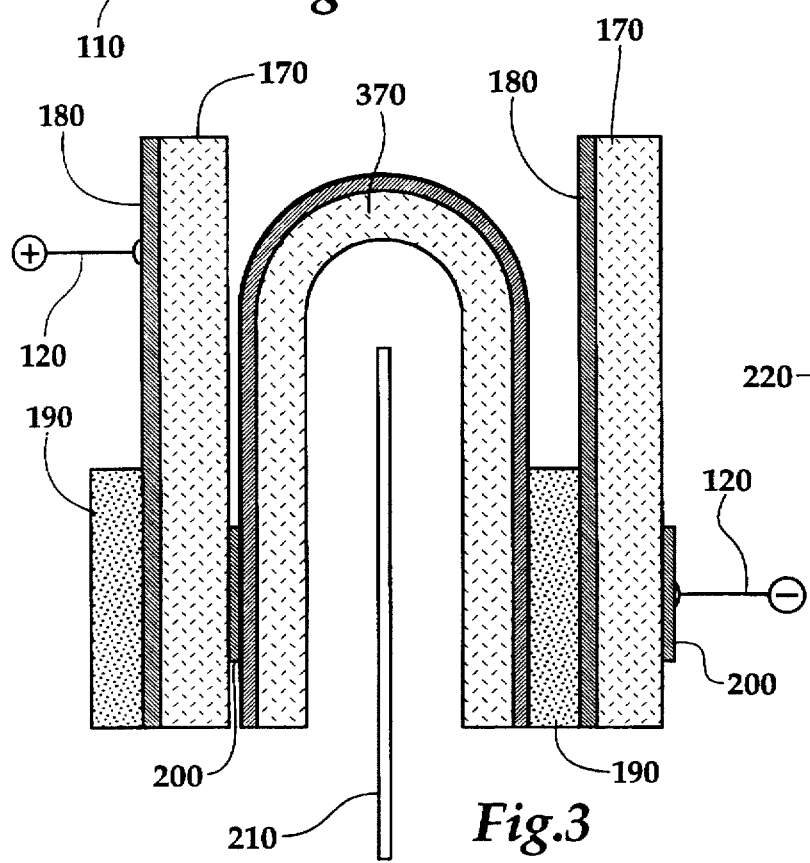
FIG. 3 is a cross-sectional view of two sensors arranged in series according to a preferred embodiment of the invention.

FIG. 3 is a lateral view of another embodiment 220 of the present invention wherein two of the sensors are arranged in series. The reference numbers often represent the same elements, although in this embodiment there are two: 170 refers to the filter paper coated with the conductor 180 such as gold on the outside (i.e. on the $MnO_2$ side); 190 refers to the oxidized substance; and 200 refers to the reduced metal. 370 refers to folded filter paper coated on the outside with a conductor 180 such as gold. Any suitable conductor could be used in place of this gold coated filter paper 370, to connect the two cells. 210 refers to a plastic sheet that prevents the electrolyte to be exchanged between the cells. This plastic sheet 210 is not necessary if multiple sensors are not arranged in series or if an electrical conduit other than the gold coated filter paper 370 is used that prevents the exchange of electrolyte between the cells. The "–" electrical conduits 120 is preferably attached to the reduced metal 200 and the "+" electrical conduit 120 is preferably attached to the conductive side of filter paper 170.

It has been found that a potentially unlimited number of the sensors 110 can be arranged in series to achieve the desired output voltage. With two in series as shown in FIG. 3, as the output voltage went up to about 3.0 volts the short circuit current when wet is between about 30 mA and 150 mA. This is more than enough to power the integrated circuit/piezoelectric speaker of the invention.

Figure 4A:
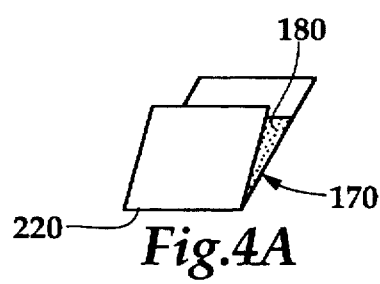
FIG. 4a is a perspective view of the absorbent paper used in the electrochemical cell of a preferred embodiment of the present invention, partially folded.
Figure 4B:
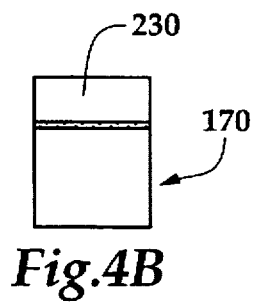
FIG. 4b is a plan view of the absorbent paper used in the electrochemical cell of a preferred embodiment of the present invention, fully folded.
Figures 5A, 5B, 5C, 5D, 5E:
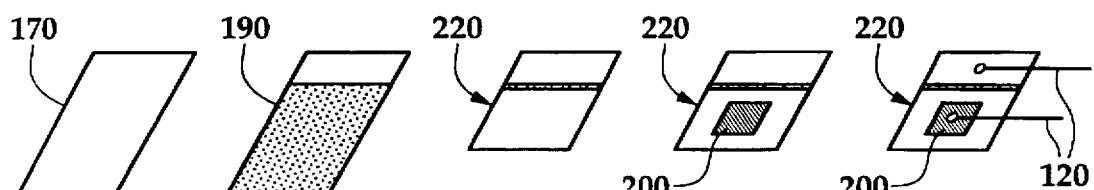
FIGS. 5a–e are perspective views of the electrochemical cell of the present invention, depicting sequentially the steps of making a pocket type sensor according to a preferred embodiment of the invention.

FIGS. 4 and 5 depict a preferred method of making another embodiment of a sensor according to the present invention. In FIG. 4a, the filter paper 170 is shown with the conductor 180 already applied and a fold 220 has been made such that only some of the conductor coated side remains exposed as can be seen as 230 in FIG. 4b. FIGS. 5a–5c again depict the coating and folding of the filter paper 170. In FIG. 5b some of the mixture 190 containing the oxidized material has been applied to less than all of the side that is coated with gold. The oxidized material can, of course, also be put into the pocket after the paper is folded. Only a few grains are necessary. FIG. 5c shows the sensor folded and the glued shut. FIG. 5d shows the sensor folded and the reduced metal 200 glued in place on the outside of the pocket, on top of the non-conducting face of the filter paper. FIG. 5e shows the sensor folded, the metal 200 in place and the electronic conductors 120 also applied. The width of the filter paper along the fold can be quite small. Depending on the application, it might be from a few microns to more than one centimeter. A sensor of the present invention with these dimensions will produce from about 1.5 volts to about 1.7 volts which is enough to power a typical integrated circuit/buzzer as described above. The overall dimensions should be as small as is possible ultimately depending upon the power requirements. Determination of the power requirements will be dictated by the current and voltage necessary to operate the chosen informing device (transducer, etc.) and the length of time it must operate. Such requirements are well known in the art. Piezoelectric buzzers of the type used in one embodiment of the invention require about 19 mA of peak current.

Figure 6:
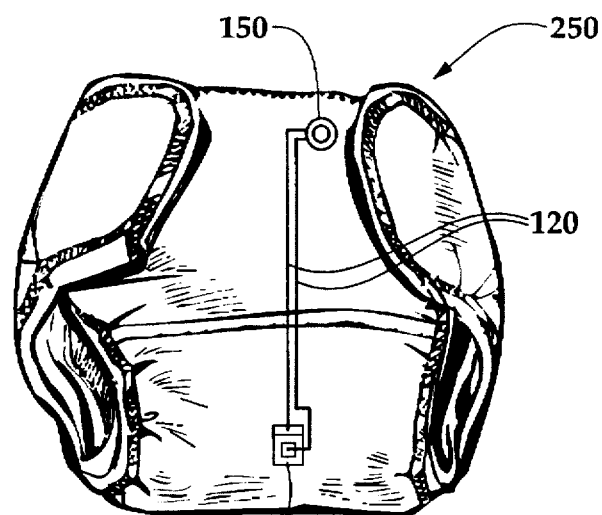
FIG. 6 is a perspective view a moisture detector according to a preferred embodiment of the invention, installed in a diaper.

FIG. 6 shows the moisture detector installed in an undergarment 250. In this embodiment, the sensor 110 is embedded in the absorbent material of the undergarment in a position where moisture collects first. This may vary depending on the sex of the wearer. Additionally, another embodiment of the invention (not shown) would use two or more sensors 110, one each for area of concern. For example, one sensor could be positioned to detect urine and one for fecal discharge. The electrical conduits 120 conduct the current developed when the sensor(s) becomes wet to the informing device 150 and are also within the absorbent material or between the absorbent material and the outer liner. The informing device is shown fashioned into a button that can be used to secure the undergarment 250 to the wearer. It can, however, be attached to the undergarment by a clip, pin, VELCRO™ or by any other permanent or temporary attachment technique known in the art. If a temporary or reversible attachment technique is employed, contacts can be used that connect the informing device 150 to the electrical conduits 120 by virtue of their relative positions rather than requiring the installer to plug the conduits 120 into the informing device. In this way, the overall cost of the device can be reduced by using one informing device for several undergarments although the sensor and electrical conduits could be disposed of along with the undergarment.

Figure 7:
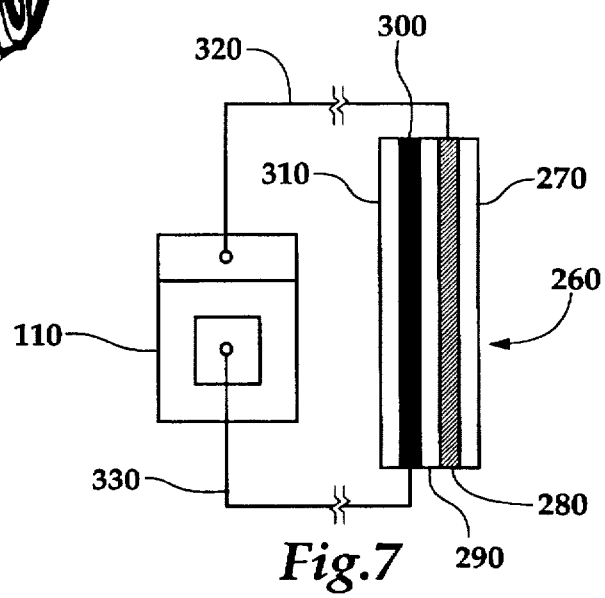
FIG. 7 is a perspective view of a moisture detector in accordance with the present invention, including an electrochromic informing means.

FIG. 7 depicts another embodiment of the present invention wherein the informing means is an electrochromic device 260. The electrochromic device turns from a reflective silver appearance to a grey-black when voltage is present. This is an irreversible (one time use) change in appearance, so that the electrochromic informing means can be permanently attached to and disposed along with the garment. It is also advantageous because when the electrochromic informing device changes color, it remains a permanent indicator of a wet condition, even after the sensor/electrochemical cell is completely discharged.

The electrochromic device is generally a sandwich of several layers. The viewing side is covered by a layer of transparent material such as a clear plastic sheet 270. On the inner side of the plastic sheet 270 is a thin layer of easily oxidizable metal 280, such as silver, copper, zinc, aluminum or chromium, for example. The next layer 290 is a clear solid electrolyte, preferably polyvinyl alcohol-phosphoric acid that appears similar to a sheet of plastic. Alternatively, the layer 290 may be a paste of polyvinyl alcohol-phosphoric acid containing titanium dioxide. The last two layers comprise a paper or plastic sheet 310 with a coating of a conductive material 300 such as carbon paste on the inner surface. Plastic sheet 310 may be replaced by ITO coated glass or plastic with a layer of tungsten trioxide as an electrochromic material substituted in place of the carbon paste 300.

When the sensor becomes wet and produces current, the current is conveyed by the positive lead 320 to the silver layer 280 and by the negative lead 330 to the conductive coating 300. This results in the oxidation of the silver, dissolving it and revealing the carbon counter electrode 300. Accordingly, when the sensor remains dry the silver layer is visible but when the sensor becomes wet and produces current, this dissolves the silver, revealing the darker and less reflective black layer indicating to the wearer or attendant that there is a wet condition. Alternatively, if ITO coated glass or plastic with a layer of tungsten trioxide as an electrochromic material is substituted in place of the carbon paste 300, the tungsten trioxide will will change color when voltage is applied, and will be visible through through ITO coated glass or plastic.

Figure 8:
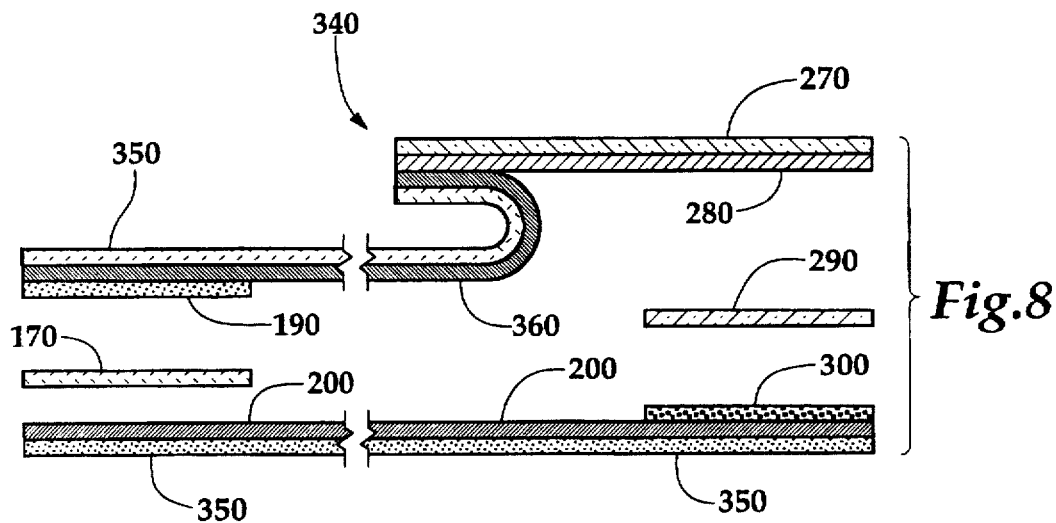
FIG. 8 is an exploded view of a moisture detector according to a preferred embodiment depicting a combined sensor and electrochromic informing device.

FIG. 8 is an exploded view of another embodiment of the invention 340 wherein the sensor and the informing means are combined into a unitary device. In this device, the sensor and informing means are connected by functional elements of the sensor instead of typical electrical conduits 120 (see FIG. 1) such as wires. In the embodiment shown in FIG. 8 the informing means is an electrochromic device similar to that shown in FIG. 7.

The sensor embodiment shown in FIG. 8 is essentially of a sandwich type construction having filter paper or another suitable porous material as the outer layers 350. The reduced chemical 200, such as zinc, and the oxidized chemical 190 are interior to the filter paper layers 350 and separated by another porous layer 170. The reduced chemical is extended along one of the outer layers 350 to conduct current produced by the sensor to the informing device. The outer layer 350 also serves as one of the outer layers of the informing device. The other conductor 360 extends from between the outer filter paper layer 350 and the reduced material 190 along the filter paper to a point where the filter paper and the conductor 360 are folded back on themselves so that the conductor is facing to the outside. The conductor can be any appropriate material such as evaporated gold. This conductor 360, exposed to the outside, is contacted by inner 280 of the first two layers of the electrochromic informing device. This inner layer 280 is a thin layer of silver disposed onto the inner surface of a clear plastic sheet 270. The next layer 290 is a clear solid electrolyte, preferably polyvinyl alcohol-phosphoric acid that appears similar to a sheet of plastic. The next layers comprise filter paper 350 coated on the inner surface with the reduced material 200 that are also the outer layers of the sensing device. Between the electrolyte 290 and the reduced chemical 200 is a coating of a conductive material 300 such as carbon paste.

When the sensor becomes wet and produces current, the current is conveyed by the conductor 360 to the silver layer 280 and by the reduced chemical 200 to the conductive coating 300. This results in the oxidation of the silver, dissolving it and revealing the carbon counter electrode 300. Accordingly, when the sensor remains dry the silver layer is visible but when the sensor becomes wet and produces current, this dissolves the silver, revealing the darker and less reflective black layer indicating to the wearer or attendant that there is a wet condition.

The length of the filter paper/gold conductor and the filter paper/zinc conductor is determined by where the informing device is to be placed. It could be on or seen through the outer pant of the undergarment near the sensing device or up near the belt line. In one embodiment the gold and zinc conductors are "painted" onto one of the layers of the undergarment along the route between the sensor and the informing means.

In another embodiment, the invention can be used to detect a wet condition in or around a life vest or other floatable emergency devices such as life rafts and seat cushions of an airplane. If the detector becomes wet as when the wearer has been forced to leave the plane or boat, it can cause a location device which is well known in the art and need not be described further here, such as a strobe, to operate.

Although preferred embodiments of the invention have been illustrated in the accompanying drawings and described in the foregoing detailed description, it will be understood that the invention is not limited to the embodiment disclosed, but is capable of numerous rearrangements and modifications of parts and elements without departing from the spirit of the invention.

We claim:

1. A moisture detector for garments comprising:
   a moisture-activated electrochemical cell including the pre-reaction members:
   a porous separator having a first side and a second side, said separator having a conductive coating on at least one of the sides,
   a substantially oxidized chemical compound attached to the first side of the separator, and
   a metal coating attached to the second side of the separator; and
   an informing means for indicating when the electrochemical cell is activated, said informing means electrically connected to and solely powered by the electrochemical cell.

2. The moisture detector according to claim 1 wherein the informing means is a piezoelectric speaker.

3. The moisture detector of claim 2 wherein the informing means further comprises an integrated circuit electrically connected to the piezoelectric speaker, the integrated circuit being capable of generating a musical signal.

4. The moisture detector according to claim 1 wherein the informing means is a light source.

5. The moisture detector according to claim 1 wherein the informing means is an electrochromic indicator.

6. The moisture detector of claim 1 wherein the conductive coating on the separator is a conductor selected from the group consisting of carbon, gold, platinum and chromium and mixtures thereof.

7. The moisture detector of claim 1 wherein the substantially oxidized chemical compound is a mixture of $MnO_2$, carbon, $KHSO_4 \cdot xH_2O$ and a glue.

8. The moisture detector of claim 1 wherein the substantially oxidized chemical compound is a mixture of $KH_2PO_4 \cdot xH_2O$ and a glue.

9. The moisture detector of claim 1 wherein the metal coating attached to the second side of the separator is a metal selected from the group consisting of zinc and aluminum and mixtures thereof.

10. The moisture detector of claim 1 wherein the porous separator is a microfiltration separator.

11. A moisture detector for garments comprising:
    a moisture-activated electrochemical cell including the pre-reaction members:
    a porous separator having a first side and a second side, the separator being folded to form a pocket such that the first side is on the inner surface of the pocket, a conductive coating on said first side of said porous separator, a substantially oxidized chemical compound disposed in the pocket, a metal coating attached to the second side of said porous separator; and an informing means for indicating when the electrochemical cell is activated, said informing means electrically connected to and solely powered by the electrochemical cell.

12. The moisture detector of claim 11 wherein the conductive coating is a conductor selected from the group consisting of carbon, gold, platinum and chromium and mixtures thereof.

13. The moisture detector of claim 11 wherein the substantially oxidized chemical compound is a mixture of $MnO_2$, carbon, $KHSO_4 \cdot xH_2O$ and a glue.

14. The moisture detector of claim 11 wherein the substantially oxidized chemical compound is a mixture of $KH_2PO_4 \cdot xH_2O$ and a glue.

15. The moisture detector of claim 11 wherein the metal coating attached to the second side of the separator is a metal selected from the group consisting of zinc and aluminum and mixtures thereof.

16. The moisture detector of claim 11 wherein the porous separator is a microfiltration separator.

17. A disposable undergarment that indicates a soiled or wet condition, comprising:

a substantially water impermeable pant;

absorbent material disposed on a first side of the pant;

a moisture-activated electrochemical cell positioned within the absorbent material, said electrochemical cell including the pre-reaction members:

a porous separator having a first side and a second side, said separator having a conductive coating on at least one of the sides, a substantially oxidized chemical compound attached to the first side of the separator, and a metal coating attached to the second side of the separator; and means for informing when the electrochemical cell is activated attached to a second side of the pant, said means for informing electrically connected to and solely powered by the electrochemical cell.

18. The disposable undergarment of claim 17 wherein the conductive coating on the separator is a conductor selected from the group consisting of carbon, gold, platinum and chromium and mixtures thereof.

19. The disposable undergarment of claim 17 wherein the substantially oxidized chemical compound is a mixture of $MnO_2$, carbon, $KHSO_4 \cdot xH_2O$ and a glue.

20. The disposable undergarment of claim 17 wherein the substantially oxidized chemical compound is a mixture of $KH_2PO_4 \cdot xH_2O$ and a glue.

21. The disposable undergarment of claim 17 wherein the metal coating attached to the second side of the separator is a metal selected from the group consisting of zinc and aluminum and mixtures thereof.

22. The disposable undergarment of claim 17 wherein the porous separator is a microfiltration separator.

23. A location aid for use with an emergency flotation device, comprising:

a water-activated electrochemical cell attached to the flotation device such that the electrochemical cell becomes wet when the flotation device is being used for flotation, said electrochemical cell including the pre-reaction members:

a porous separator having a first side and a second side, said separator having a conductive coating on at least one of the sides, a substantially oxidized chemical compound attached to the first side of the separator, and a metal coating attached to the second side of the separator;

means for informing when the electrochemical cell is activated attached to the flotation device, said means for informing electrically connected to and solely powered by the electrochemical cell.

24. The location aid of claim 23 wherein the conductive coating on the separator is a conductor selected from the group consisting of carbon, gold, platinum and chromium and mixtures thereof.

25. The location aid of claim 23 wherein the substantially oxidized chemical compound is a mixture of $MnO_2$, carbon, $KHSO_4 \cdot xH_2O$ and a glue.

26. The location aid of claim 23 wherein the substantially oxidized chemical compound is a mixture of $KH_2PO_4 \cdot xH_2O$ and a glue.

27. The location aid of claim 23 wherein the metal coating attached to the second side of the separator is a metal selected from the group consisting of zinc and aluminum and mixtures thereof.

28. The location aid of claim 23 wherein the porous separator is a microfiltration separator.

* * * * *